United States Patent [19]

Jessel, Jr. et al.

[11] Plant 4,130

[45] Oct. 18, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 716,439

[22] Filed: Aug. 23, 1976

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Donald D. Jeffery

[57] ABSTRACT

This novel yellow spider chrysanthemum has the ability to produce quality blooms in spring, summer, and fall programs.

3 Drawing Figures

1

The present invention comprises a new and distinct cultivar of *Chrysanthemum morifolium,* Ramat., hereinafter referred to by the cultivar name Plume (No. 73038057).

Plume is a product of a planned breeding program which had the objective of creating new chrysanthemum cultivars with spider inflorescence type, with white or yellow inflorescence color, with 9 week flowering response, and with the ability to produce commercially acceptable quality in spring, summer and fall cut spray mum programs. Such traits in combination were not present in previously available commercial cultivars.

Plume was originated from a cross made in a controlled breeding program in Barberton, Ohio in 1972. The female, or seed parent, was White Spider 2275 (No. 21660E02; unpatented; commercially available), a white spider of parentage unknown to the present inventors. The male, or pollen parent, of Plume was Yellow Daisy Pot (No. 2168AE01; unpatented; commercially available), a yellow spooned daisy sport of White Daisy Pot (No. 21680E01; unpatented; commercially available). White Daisy Pot, a white spooned daisy, is of parentage unknown to the present inventors.

Plume was discovered and selected as one flowering plant within the progeny of the stated cross by Walter H. Jessel, Jr. and William E. Duffett on Mar. 26, 1973 in a controlled environment in Barberton, Ohio.

The first act of asexual reproduction was accomplished when vegetative cuttings were taken from the initial selection in May, 1973 in a controlled environment in Barberton, Ohio by a technician working under formulations established and supervised by Walter H. Jessel, Jr. and William E. Duffett. Horticultural examination of selected units initiated Nov. 21, 1974 has demonstrated that the combination of characteristics as herein disclosed for Plume are firmly fixed and are retained through successive generations of asexual reproduction.

Plume has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice, as described in Chart A which apears at the end of the present specification. A light intensity chart of general use is shown in ASHAE Trans., Vol. 64, pg. 64, and reference is made thereto.

2

The following traits have been repeatedly observed and are determined to be basic characteristics of Plume which in combination distinguish this chrysanthemum as a new and distinct cultivar:

1. Flat inflorescence form.
2. Spider inflorescence type.
3. Medium yellow inflorescence color, oxidizing to light yellow at maturity.
4. Diameter across face of inflorescence ranging from 90 to 140 mm. at maturity.
5. Uniform nine week photoperiodic flowering response to short days.
6. Medium plant height (requiring 1–2 long day weeks prior to short days to produce 72 to 82 cm. height when grown as a single stem plant from May through October).
7. Semi-upright branching pattern.

The accompanying photographic drawings show typical inflorescence and foliage characteristics of Plume with colors being as nearly true as possible with illustrations of this type. Sheet 1 is a color photograph of Plume. Sheet 2 is a black and white photograph showing three views of the inflorescence of Plume. Sheet 3 is a black and white photograph showing the foliage of Plume at three stages of growth.

Of the many commercial cultivars known to the present inventors, the most similar existing cultivar in comparison to Plume is Super Yellow (No. 2166BE02; unpatented). Reference is made to the attached Chart B which compares certain characteristics of Plume with those same characteristics of Super Yellow. It will be noted that Plume has darker inflorescence color, smaller diameter across face of inflorescence, taller plant height, and shorter flowering response period. The inflorescence form and inflorescence type of Plume are similar to those same characteristics of Super Yellow.

In the following description, color references are made to The Munsell Color Cascade, 1972 edition. The color values were determined between 10:00 and 10:30 A.M. on June 24, 1976 under 150 foot-candle light intensity at Barberton, Ohio.

Botanical Classification: *Chrysanthemum morifolium,* Ramat., cv Plume.

INFLORESCENCE (See Sheets 1 and 2 of drawings)

Capitulum:

*Form.*—Flat.

*Type.*—Spider.

*Permanence.*—12 to 14 days.
*Diameter across face.*— 90 to 140 mm.

B. Corolla of Ray Florets:
*Color (abaxial).*—25-6 to 25-2.
*Color (immature center)*—22-6.
*Color (adaxial).*—25-4 to 25-2.

C. Reproductive Organs
*Androecium.*—Present disc florets only; scant to numerous; scant pollen.
*Gynoecium.*—Present both ray and disc florets.

Plant

General appearance; Medium height; semi-upright branching pattern.

Foliage (See Sheets 1 and 3 of drawings.):
*Color (abaxial).*—20-15.
*Color (adaxial).*—20-14 overlaid with white.

We claim:

1. A new and distinct cultivar of *Chrysanthemum morifolium,* Ramat. plant known by the cultivar name Plume and particularly characterized as to uniqueness by the combined characteristics of flat inflorescence form; spider inflorescence type; medium yellow inflorescence color, oxidizing to light yellow at maturity; diameter across face of inflorescence ranging from 90 to 140 mm. at maturity; uniform nine week photoperiodic flowering response to short days; medium plant height; and semi-upright branching pattern.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7-10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7-10 f.c. | NONE | 300 ppm |
| SPRING | 58° F to 65° F | 65° F to 80° F | 60° F to 75° F | 2 to 4 weeks at 5 Hours Per Night of 7-10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7-10 f.c. | on - 6:00 PM Off - 8:00 AM | NONE |

CHART B

COMPARISON OF PLUME AND SUPER YELLOW

| CULTIVAR | INFLORESCENCE COLOR | INFLORESCENCE FORM AND TYPE | DIAMETER ACROSS FACE OF INFLORESCENCE | PLANT HEIGHT | FLOWERING RESPONSE PERIOD |
|---|---|---|---|---|---|
| Plume | Medium yellow | Flat spider | 90 to 140 mm. | Medium | 9 week |
| Super Yellow | Light yellow | Flat spider | 100 to 150 mm. | Short | 10 week |

COMPARISONS MADE OF PLANTS GROWN IN A GREENHOUSE IN BARBERTON, OHIO UNDER CONDITIONS AS DESCRIBED IN CHART A.

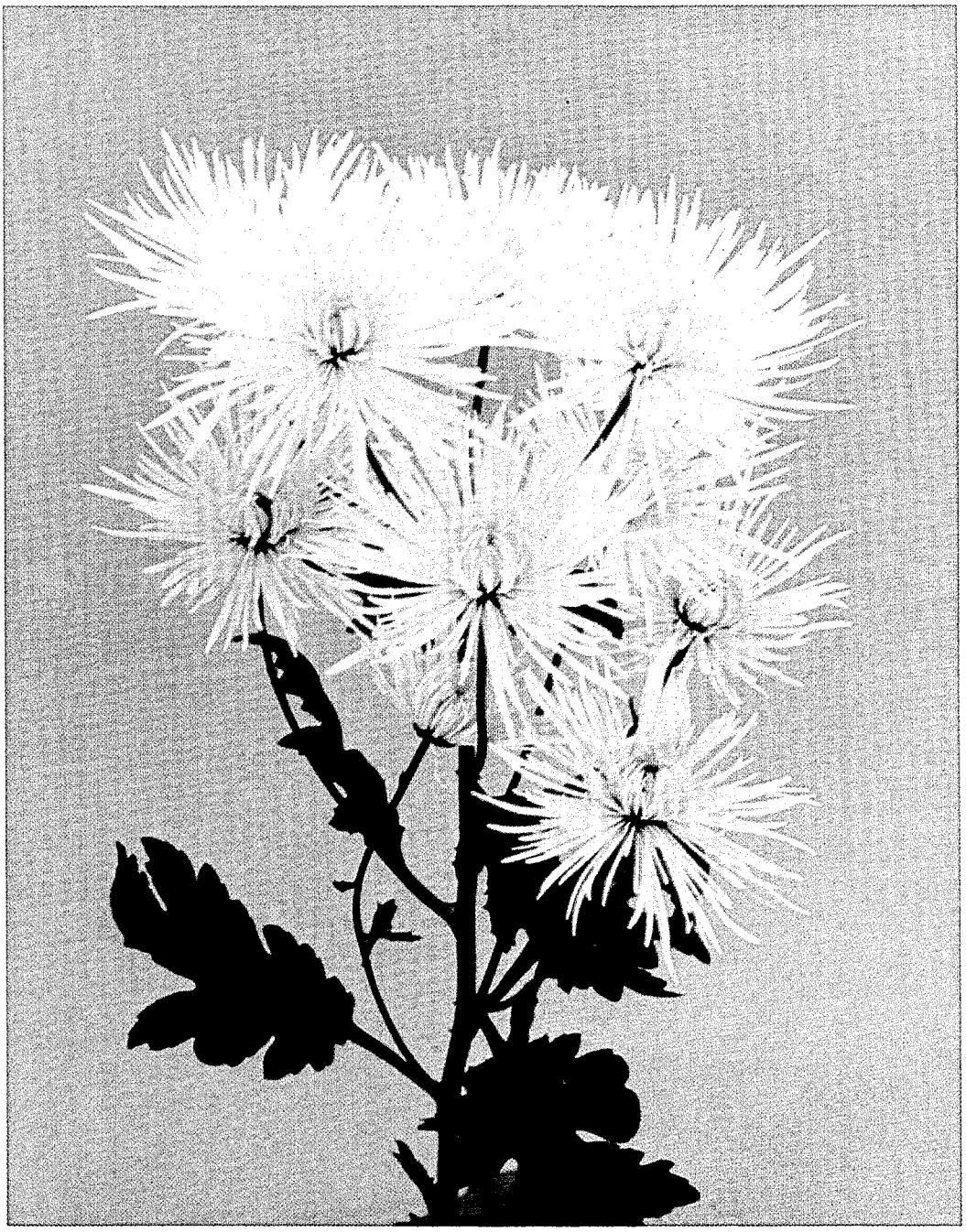

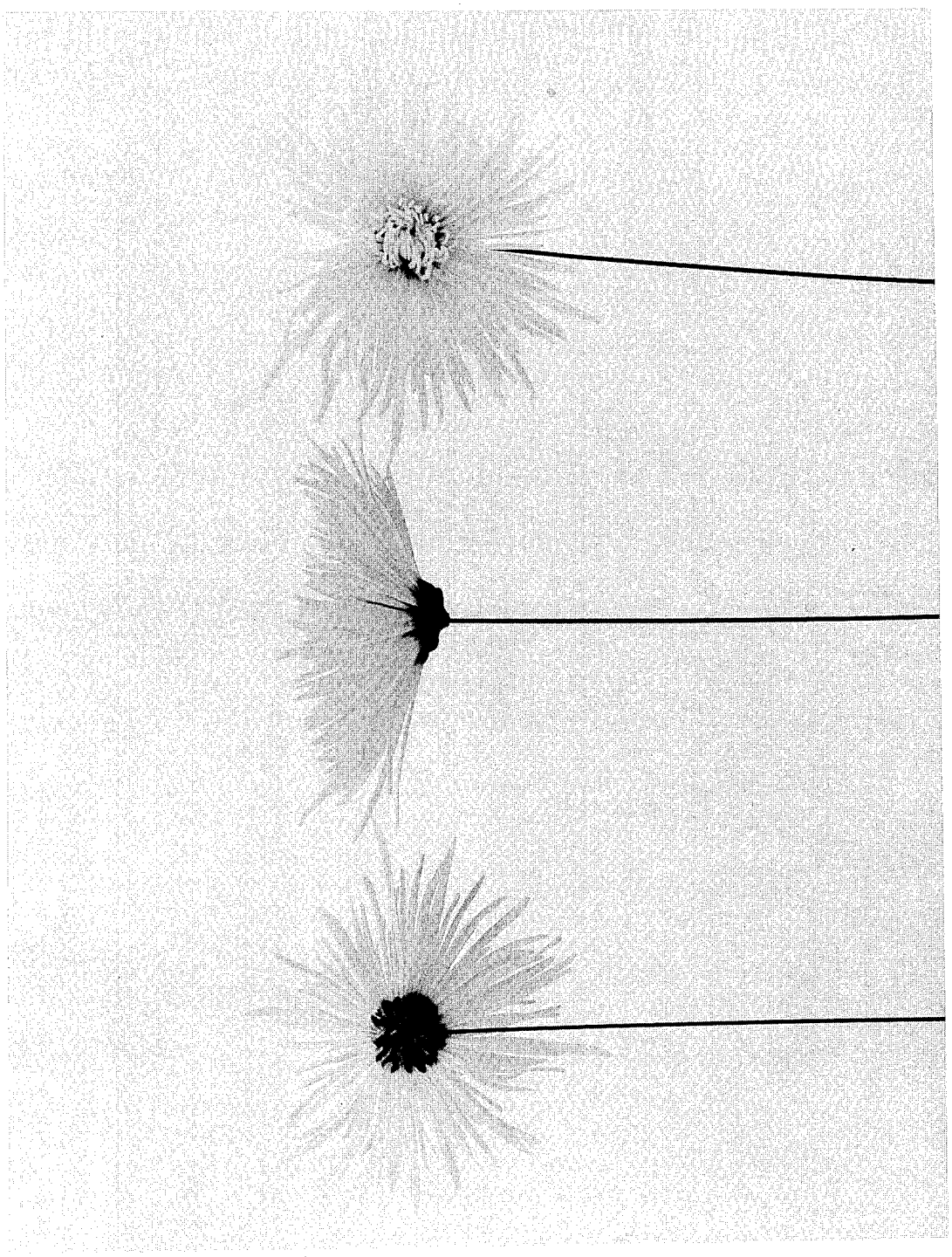

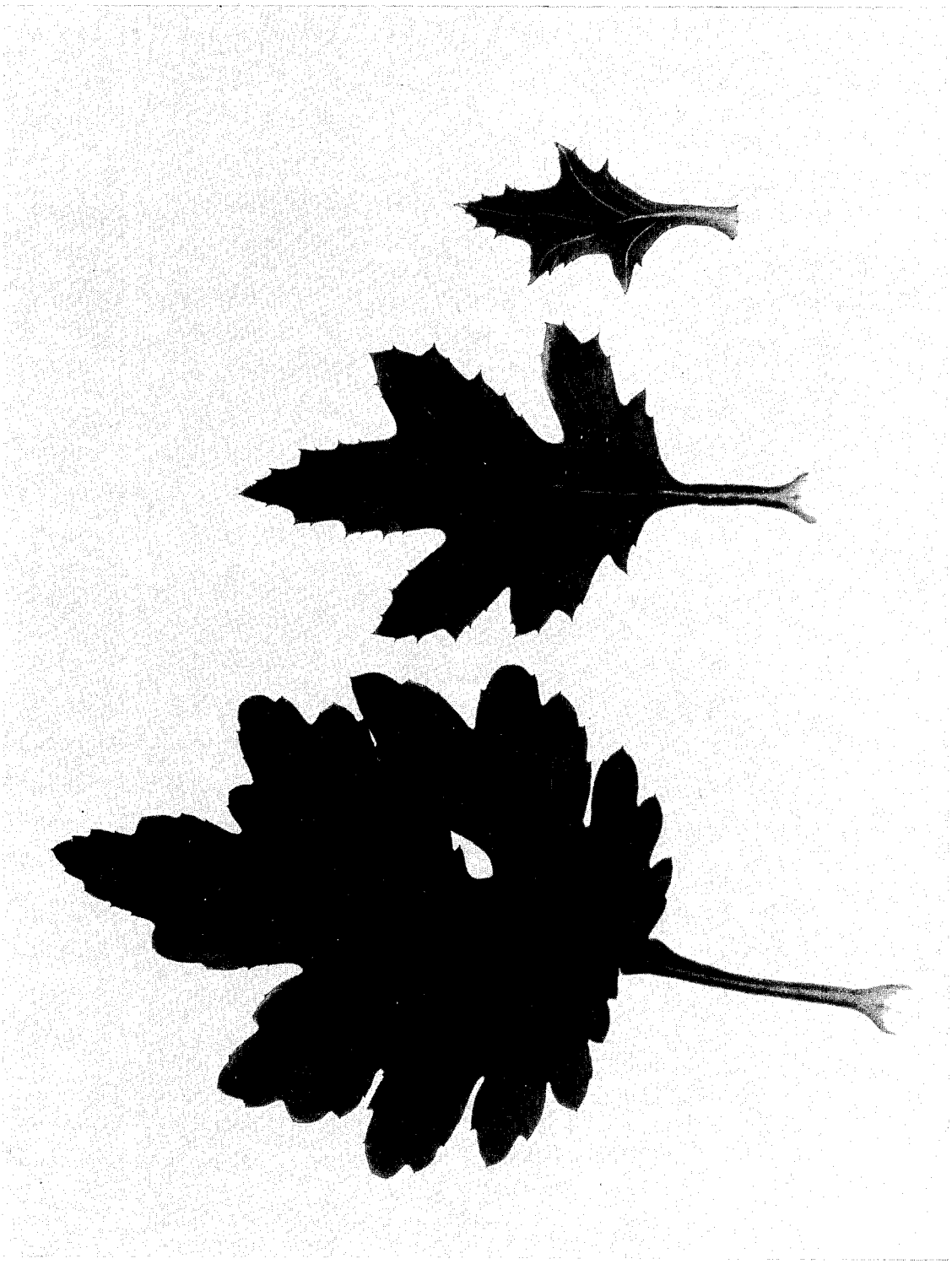

* * * * *